United States Patent
Shirahama et al.

(10) Patent No.: US 11,844,681 B2
(45) Date of Patent: Dec. 19, 2023

(54) STENT GRAFT WITH A POSITION ADJUSTMENT PORTION

(71) Applicant: SB-KAWASUMI LABORATORIES, INC., Kanagawa (JP)

(72) Inventors: Noriaki Shirahama, Oita (JP); Takashi Yoshimori, Oita (JP)

(73) Assignee: SB-KAWASUMI LABORATORIES, INC., Kanagawa (JP)

( * ) Notice: Subject to any disclaimer, the term of this patent is extended or adjusted under 35 U.S.C. 154(b) by 105 days.

(21) Appl. No.: 17/276,181

(22) PCT Filed: Sep. 20, 2019

(86) PCT No.: PCT/JP2019/036915
§ 371 (c)(1),
(2) Date: Mar. 15, 2021

(87) PCT Pub. No.: WO2020/066874
PCT Pub. Date: Apr. 2, 2020

(65) Prior Publication Data
US 2022/0039939 A1    Feb. 10, 2022

(30) Foreign Application Priority Data
Sep. 27, 2018 (JP) .................................. 2018-182618

(51) Int. Cl.
*A61F 2/07* (2013.01)
*A61F 2/06* (2013.01)

(52) U.S. Cl.
CPC .......... *A61F 2/07* (2013.01); *A61F 2002/065* (2013.01)

(58) Field of Classification Search
CPC ........ A61F 2002/065; A61F 2/07; A61F 2/89; A61F 2002/061; A61F 2250/0006; A61F 2/954; A61F 2/856
See application file for complete search history.

(56) References Cited

U.S. PATENT DOCUMENTS

| | | | | |
|---|---|---|---|---|
| 5,709,713 A | * | 1/1998 | Evans | A61F 2/07 623/1.53 |
| 6,030,414 A | * | 2/2000 | Taheri | A61F 2/856 623/1.1 |

(Continued)

FOREIGN PATENT DOCUMENTS

| | | |
|---|---|---|
| JP | 2012-525227 | 10/2012 |
| JP | 2013-071005 | 4/2013 |

(Continued)

OTHER PUBLICATIONS

International Search Report and the Written Opinion dated Nov. 5, 2019 From the International Searching Authority Re. Application No. PCT/JP2019/036915 and Its Translation of Search Report Into English. (12 Pages).

*Primary Examiner* — Jerrah Edwards
*Assistant Examiner* — Mindy Thuy Huynh

(57) ABSTRACT

The stent graft (10) is to be placed in a tubular tissue and is equipped with: a skeleton portion (11); a tubular graft portion (12) having, in part of a tube wall, a side opening (opening 121a of branch portion 121) that communicates with the lumen, the graft portion being provided along the skeleton portion; and a position adjustment portion (13) capable of adjusting the relative position of the side opening in the graft portion when the stent graft is placed in the tubular tissue.

10 Claims, 5 Drawing Sheets

(56) References Cited

U.S. PATENT DOCUMENTS

| | | | |
|---|---|---|---|
| 8,540,764 B2* | 9/2013 | Bruszewski | A61F 2/07 623/1.13 |
| 8,870,939 B2* | 10/2014 | Roeder | A61F 2/856 623/1.13 |
| 9,649,188 B2* | 5/2017 | Hartley | A61F 2/07 |
| 9,662,196 B2* | 5/2017 | Roeder | A61F 2/07 |
| 10,485,684 B2* | 11/2019 | Marmur | A61F 2/91 |
| 2002/0193873 A1* | 12/2002 | Brucker | A61F 2/958 623/1.35 |
| 2005/0102021 A1* | 5/2005 | Osborne | A61F 2/07 623/1.13 |
| 2005/0131517 A1* | 6/2005 | Hartley | A61F 2/07 623/1.13 |
| 2007/0244547 A1* | 10/2007 | Greenan | A61F 2/07 623/1.35 |
| 2011/0054586 A1 | 3/2011 | Mayberry et al. | |
| 2011/0270378 A1 | 11/2011 | Bruszewski et al. | |
| 2011/0313512 A1 | 12/2011 | Hartley et al. | |
| 2013/0079870 A1 | 3/2013 | Roeder et al. | |

FOREIGN PATENT DOCUMENTS

| | | |
|---|---|---|
| JP | 5789867 | 8/2015 |
| JP | 2018-051259 | 4/2018 |

\* cited by examiner

US 11,844,681 B2

STENT GRAFT WITH A POSITION ADJUSTMENT PORTION

TECHNICAL FIELD

The present invention relates to a stent graft.

BACKGROUND ART

Conventionally, a branch vessel stent graft is known as a stent graft used for the treatment of aortic aneurysms, aortic dissections, or the like caused in the aorta (e.g. see Patent Document 1). This branch vessel stent graft has a side opening leading to a branch vessel, on a tube wall of a tubular graft portion.

For example, while a branch vessel-compatible main vessel stent graft is placed in a main vessel, the branch vessel stent graft is connected to the side opening, and the branch vessel stent graft is placed in the branch vessel, so that a bloodstream between the main vessel and the branch vessel can be maintained.

PRIOR ART DOCUMENT

Patent Document

Patent Document 1: Japanese Patent Publication No. 5789867

SUMMARY OF THE INVENTION

Technical Problem

To properly place a branch vessel stent graft in a branch vessel, it is desirable to place a main vessel stent graft such that displacement between a vessel opening of the branch vessel and a side opening of a main vessel stent graft is minimized. However, there is an individual difference in a position of the vessel opening of the branch vessel among patients, and a position of the side opening of the main vessel stent graft also varies depending on a mounting state, and therefore skill and experience of an operator greatly affect alignment between the vessel opening of the branch vessel and the side opening of the main vessel stent graft.

In addition, depending on the position, orientation or the like of the side opening of the main vessel stent graft placed in the main vessel, there are risks that it becomes difficult to connect the branch vessel stent graft to the side opening, and further the branch vessel stent graft cannot be properly placed in the branch vessel.

An object of the present invention is to provide a stent graft that allows preferable alignment between a side opening of a stent graft for a main tubular tissue (e.g. a main vessel) and a branch opening of a branch tubular tissue (e.g. a vessel opening of a branch vessel).

Solution to Problem

The stent graft according to the present invention is a stent graft to be placed in a tubular tissue, including
 a skeleton portion,
 a tubular graft portion disposed along the skeleton portion, and having a side opening leading to a lumen in a part of a tube wall,
 position adjustment portions capable of adjusting a relative position of the side opening on the graft portion in a state where the stent graft is placed in the tubular tissue.

Advantageous Effect of the Invention

The present invention makes it possible to perform preferable alignment between a side opening of a main tubular tissue stent graft and a branch opening of a branch tubular tissue.

DESCRIPTION OF THE EMBODIMENT

Hereinafter, an embodiment of the stent graft according to the present invention will be explained in detail with reference to the drawings.

In this embodiment, a case where a first stent graft 10 to which the present invention is applied is placed in a main vessel V1, and a second stent graft 50 is connected to the first stent graft 10 and placed in the branch vessel V2 will be explained. (see FIG. 4A and FIG. 4B).

Figure 1A:
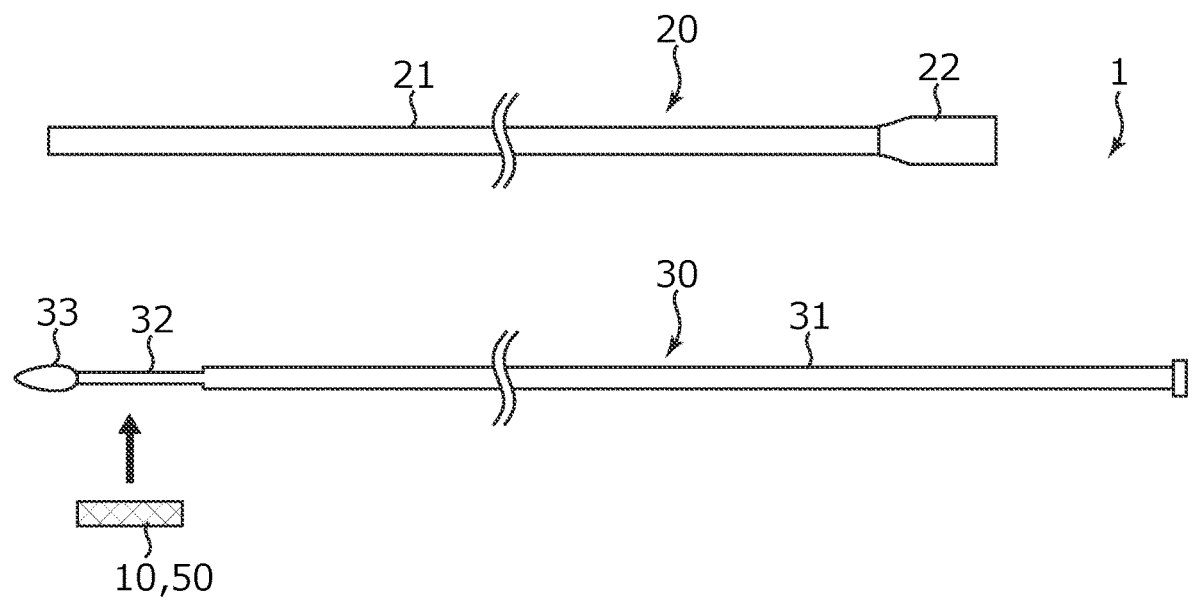
FIG. 1A is a diagram illustrating a configuration of a stent graft placement device.
Figure 1B:
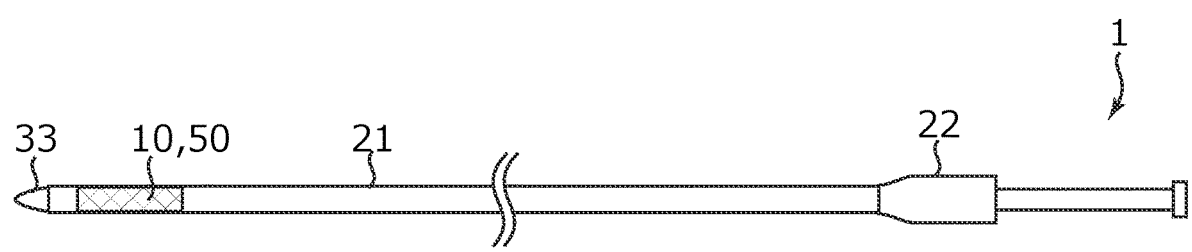
FIG. 1B is a diagram illustrating the configuration of the stent graft placement device.

FIG. 1A and FIG. 1B are diagrams illustrating a configuration of a stent graft placement device 1. FIG. 1A illustrates a state that the stent graft placement device 1 is disassembled, and FIG. 1B illustrates a state that the stent graft placement device 1 is assembled. In FIG. 1A and FIG. 1B, a size (length, diameter, etc.), a shape, and the like of each member constituting the stent graft placement device 1 are schematically illustrated for the purpose of facilitating understanding of the invention.

The stent graft placement device 1 is used for placing the first stent graft 10 and the second stent graft 50 in a blood vessel. In the following description, a case where the first stent graft 10 is placed in a blood vessel will be explained as an example.

As illustrated in FIG. 1A and FIG. 1B, the stent graft placement device 1 includes a tubular sheath 20, an inner rod 30 disposed inside the sheath 20 and configured to advance and retreat along an axial direction (longitudinal direction) of the sheath 20 in the sheath 20, and the first stent graft 10 accommodated in the sheath 20 so as to be expandable in a radial direction. When the second stent graft 50 is placed in a blood vessel, the second stent graft 50, instead of the first stent graft 10, is accommodated in the sheath 20.

The sheath 20 has a tubular sheath main body portion 21, and a hub 22 disposed on a proximal end side (right side in FIG. 1A and FIG. 1B) of the sheath main body portion 21. Although not illustrated in the figures, the hub 22 has a nut for fixing the inner rod 30 to the sheath 20 or releasing the fixation.

The sheath 20 is made of a flexible material. Examples of the flexible material include a biocompatible synthetic resin (elastomer) selected from a fluororesin, a polyamide-based resin, a polyethylene-based resin, a polyvinyl chloride-based resin, etc., a resin compound in which these resins are mixed with another material, a multilayered structure made of these synthetic resins, a composite of these synthetic resins and metal wires, and the like.

The inner rod 30 includes a bar-shaped rod main body portion 31, a holding portion 32 for holding the first stent graft 10 in a contracted state, and a distal tip 33 disposed on a distal end portion (farther end portion) of the inner rod 30. A diameter of the holding portion 32 is set to be smaller than that of the rod main body portion 31 e.g. by a thickness of the first stent graft 10.

Examples of a material constituting the rod main body portion 31 and the holding portion 32 include various materials having an appropriate hardness and flexibility, such as a resin (plastic, elastomer) and a metal. Examples of a material constituting the distal tip 33 include various materials having an appropriate hardness and flexibility, such as a synthetic resin (elastomer) selected from a polyamide-based resin, a polyurethane-based resin, a polyvinyl chloride-based resin.

Although not illustrated in the figures, for example, a guide wire lumen through which a guide wire passes, a trigger wire lumen through which a trigger wire passes for expanding the contracted first stent graft 10 on a lesion, and the like are formed along an axial direction of the inner rod 30 on the rod main body portion 31, the holding portion 32, and the distal tip 33.

Figure 2A:
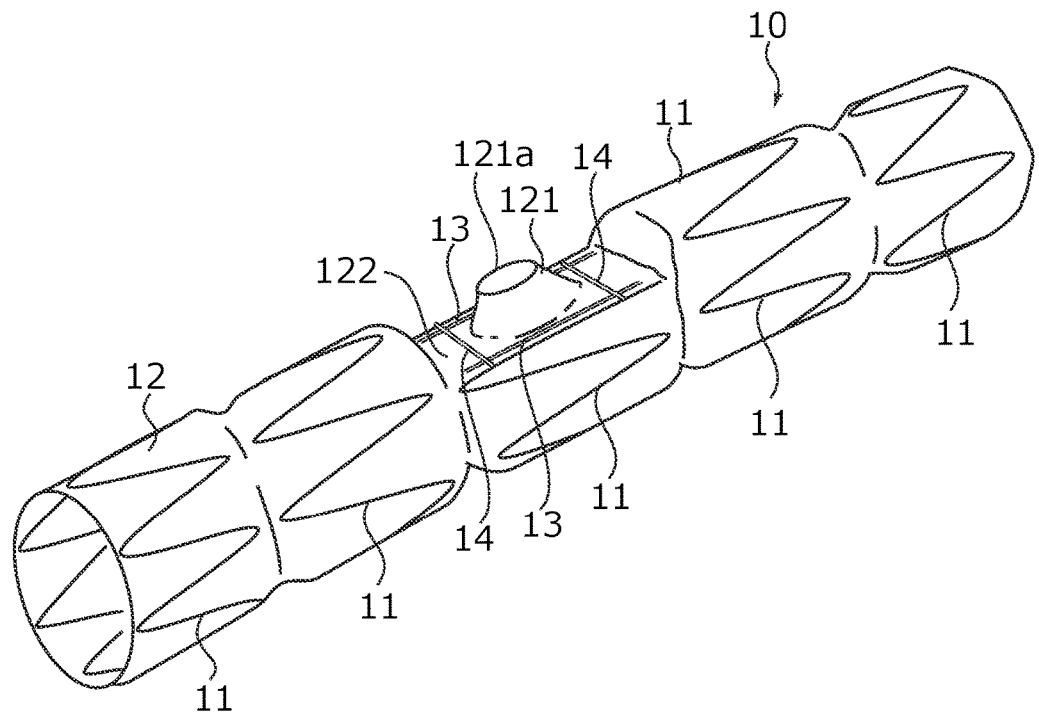
FIG. 2A is a diagram illustrating a configuration of a first stent graft.
Figure 2B:
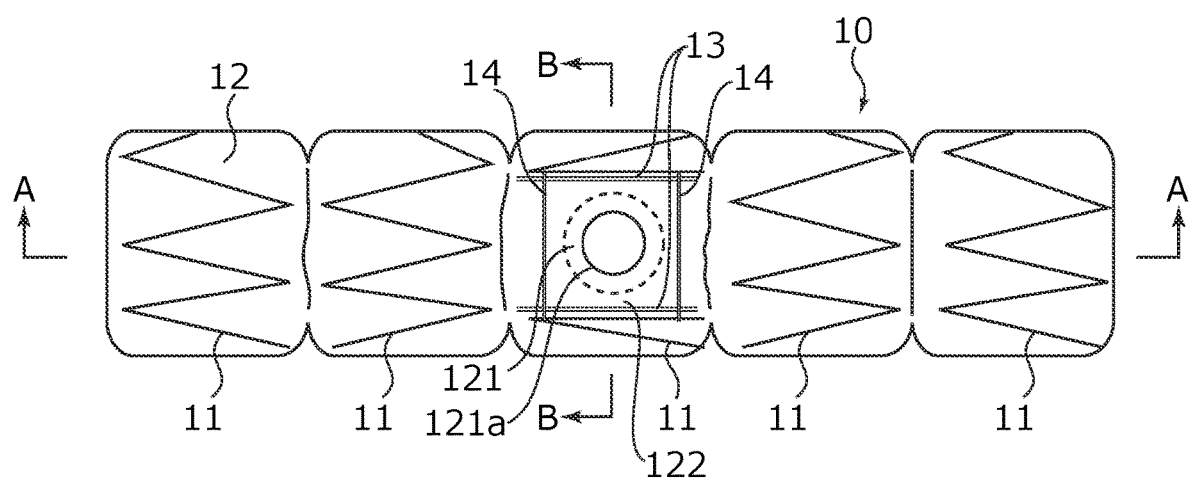
FIG. 2B is a diagram illustrating the configuration of the first stent graft.
Figure 3A:
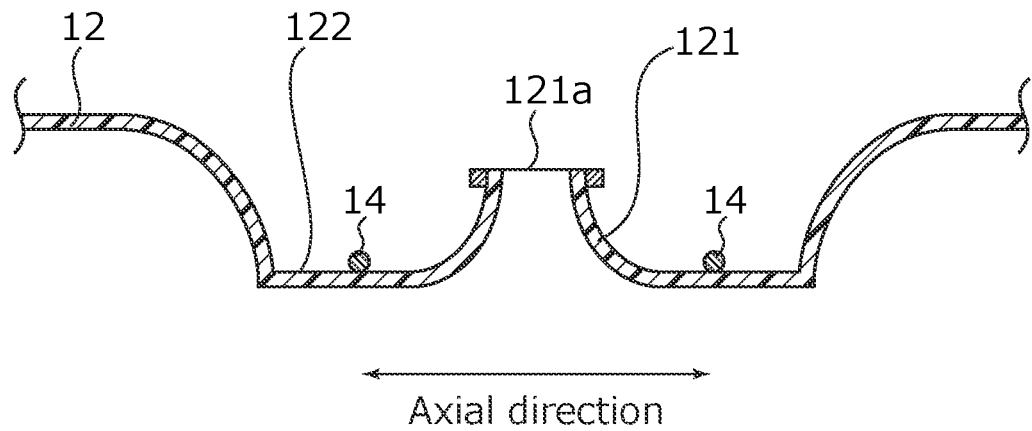
FIG. 3A is a sectional view illustrating a configuration of a branch portion of the first stent graft.
Figure 3B:
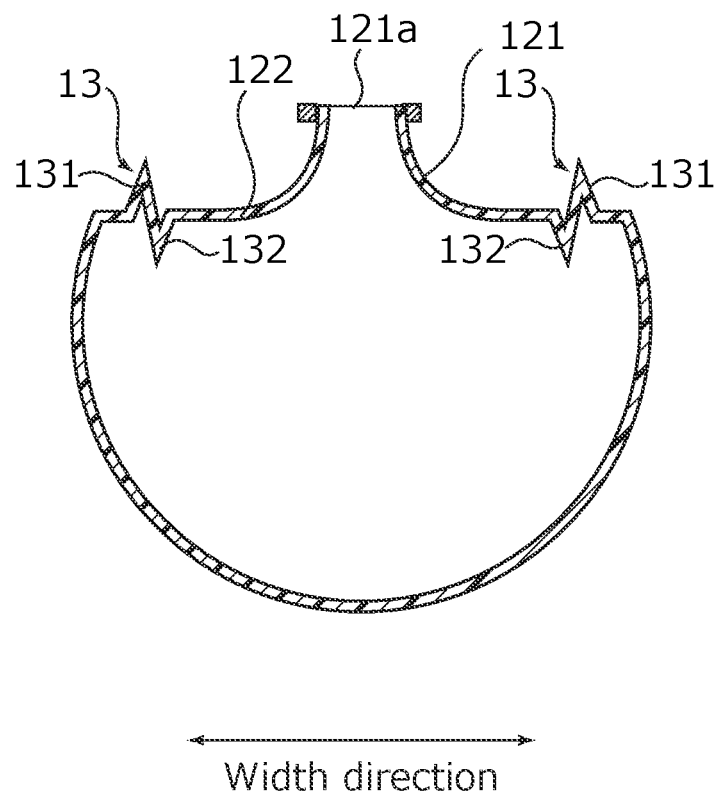
FIG. 3B is a sectional view illustrating the configuration of the branch portion of the first stent graft.

FIG. 2A is a perspective view of the first stent graft 10, and FIG. 2B is a plan view of the first stent graft 10 viewed from a branch portion 121 side. FIG. 3A is a sectional view taken along line A-A in FIG. 2B (only on the branch portion 121 side), and FIG. 3B is a sectional view taken along line B-B in FIG. 2B. In these figures, the expanded first stent graft 10 is schematically illustrated for facilitating understanding of the invention. In addition, in FIG. 3A and FIG. 3B, a skeleton portion 11 is omitted.

Figure 4A:
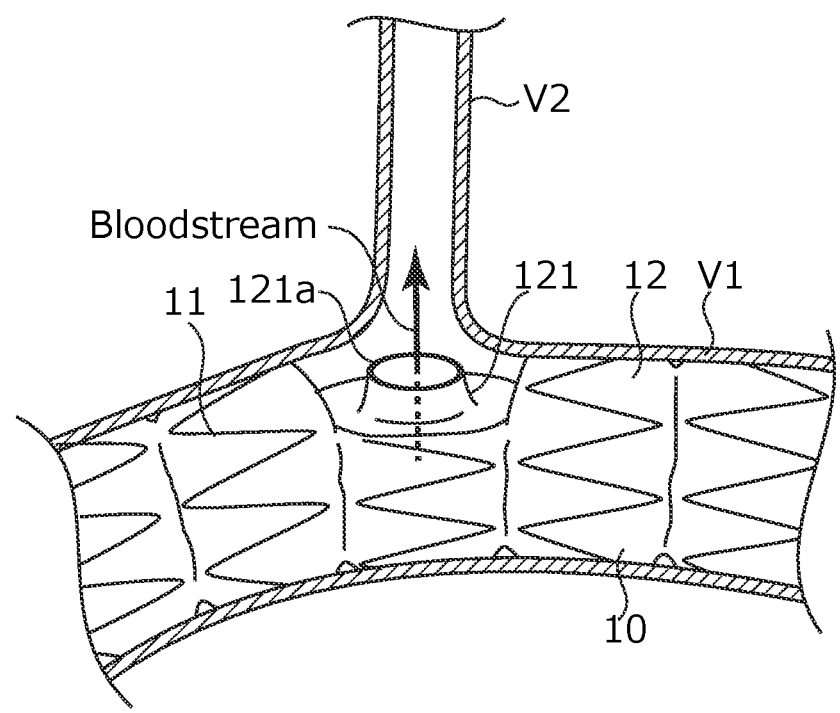
FIG. 4A is a diagram illustrating a state that the first stent graft and a second stent graft are placed in a blood vessel.
Figure 4B:
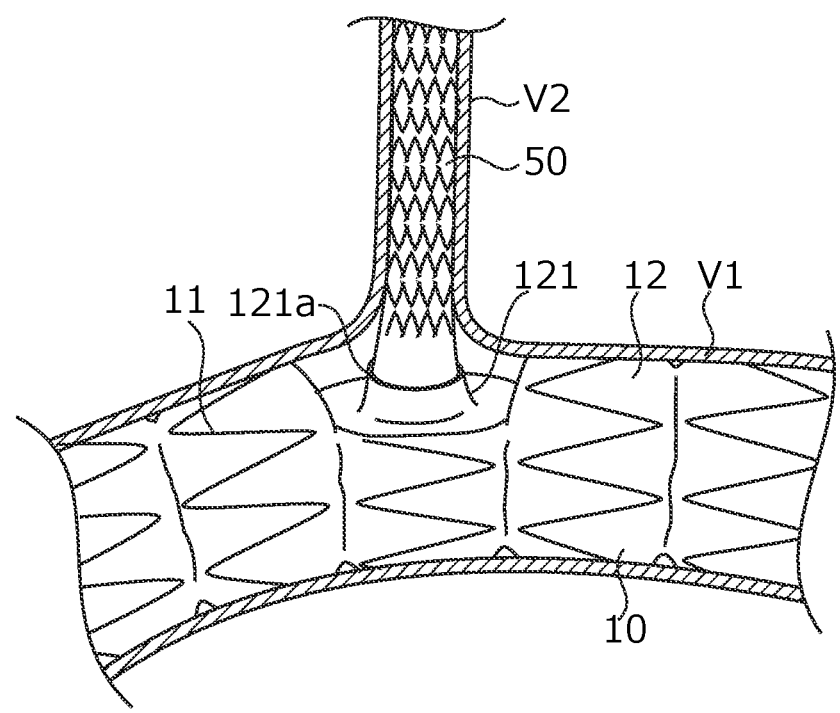
FIG. 4B is a diagram illustrating the state that the first stent graft and the second stent graft are placed in the blood vessel.

The first stent graft 10 is a branch vessel-compatible main vessel stent graft and placed in the main vessel V1 (see FIG. 4A and FIG. 4B). As illustrated in FIGS. 2A and 2B, the first stent graft 10 includes the skeleton portion 11 and a tubular graft portion 12 disposed along the skeleton portion 11. A branch portion 121 having an opening 121a (side opening) leading to a lumen of the graft portion 12 is disposed on a tube wall of the graft portion 12. While the first stent graft 10 is placed in the main vessel V1, the second stent graft 50 is connected to the branch portion 121, and the second stent graft 50 is placed in the branch vessel V2, so that a bloodstream between the main vessel V1 and the branch vessel V2 can be maintained.

In this embodiment, the case where the first stent graft 10 has a straight tube shape is described as an example, but the first stent graft 10 may have an arch shape (e.g. corresponding to a shape of an aortic arch of a patient) or a twisted detour shape.

The skeleton portion 11 is a self-expansible stent skeleton configured so as to be deformable from the contracted state that the skeleton is contracted inward in the radial direction to an expanded state that the skeleton is expanded outward in the radial direction to demarcate a tubular flow path. In this embodiment, the skeleton portion 11 is composed of five skeleton pieces formed into a tubular shape by folding thin metal wires in a zigzag pattern, and wholly has a tubular shape by arranging the skeleton pieces in parallel such that each lumen communicates with each other. The adjacent skeleton pieces may be joined to each other through a joint member.

Examples of a material of the thin metal wire for forming the skeleton portion 11 include known metals or metal alloys typified by a stainless steel, a nickel-titanium alloy, a cobalt-chromium alloy, a titanium alloy, and the like. The skeleton portion 11 may be made of a material other than metals (e.g. a ceramic, a resin, or the like).

The graft portion 12 is arranged along the skeleton portion 11 so as to cover the skeleton portion 11 to demarcate the aforementioned tubular flow path. Examples of a material for forming the graft portion 12 include a fluororesin such as PTFE (polytetrafluoroethylene), a polyester resin such as polyethylene terephthalate, and the like. The graft portion 12 is fixed to the skeleton portion 11 e.g. by saturation with a thread, sticking with a tape, adhesion, welding, or the like.

The graft portion 12 may be disposed on an outer peripheral side or an inner peripheral side of the skeleton portion 11, or may be arranged so as to sandwich the skeleton portion 11 from the outer peripheral side and the inner peripheral side.

In the graft portion 12, a part of the tube wall (substantially the axial-direction middle of the first stent graft 10 in FIG. 2A and FIG. 2B) has a concave portion 122 that is recessed inward in the radial direction. On substantially the center of the flat bottom face of the concave portion 122, a cylindrical branch portion 121 is formed so as to protrude outward in the radial direction of the graft portion 12. The branch portion 121 is made of the same material as for the graft portion 12 and formed integrally with the graft portion 12. For example, the branch portion 121 has flexibility to an extent that orientation of the opening 121a can be changed by the bloodstream from the main vessel V1 to the branch vessel V2.

Preferably, the branch portion 121 has a tapered shape whose diameter gradually decreases toward the opening 121a on the distal end side. Thereby, when the first stent graft 10 is placed in the main vessel V1 and the second stent graft 50 is connected to the branch portion 121 and placed in the branch vessel V2, adhesiveness between the first stent graft 10 and the second stent graft 50 can be improved.

Furthermore, while placed in the blood vessel, the first stent graft 10 has position adjustment portions 13 capable of adjusting a relative position of the branch portion 121 on the graft portion 12 (specifically, the position and orientation of the opening 121a of the branch portion 121).

In this embodiment, for example, the position adjustment portions 13 are configured to be deformable, and is composed of pleats formed along the axial direction on both sides of the branch portion 121 in a width direction (direction orthogonal to the axial direction) of the concave portion 122. As illustrated in FIG. 3B, the pleats are creases (gathers) sterically folded such that crest portions 131 and trough portions 132 are alternately formed, and, for example, formed by folding the bottom face of the concave portion 122 of the graft portion 12.

The pleats only need to be stretchable in a direction orthogonal to an extending direction of the pleats (crease-arranging direction, i.e. in this case, the width direction of the concave portion 122). A type of pleats (e.g. bellows-like accordion pleats, or the like) is not particularly limited. In addition, as illustrated in FIG. 3B, the pleats may have a shape that the crest portions 131 and the trough portions 132 are formed on both sides so as to travel across the bottom face of the concave portion 122, or a shape that only the crest portion 131 or only the trough portion 132 is formed on the one side of the bottom face of the concave portion 122. In addition, the pleats may have a plurality of crest portions 131 and/or trough portions 132, and in this case, the crest portions 131 and the trough portions 132 may be alternately and continuously formed, or the crest portions 131 or the trough portions 132 may be continuously formed. Also, the pleats include a shape that only one of the crest portion 131 or the trough portion 132 is formed.

For example, when a guide wire 40 (see FIG. 5C) or the sheath 20 abuts on the branch portion 121 and a resulting external force acts on the branch portion 121, the position adjustment portions 13 easily expand or contract in the arrangement direction of the creases of the pleats. Accompanying the expansion or contraction (deformation) of the position adjustment portions 13, the branch portion 121 is displaced in the width direction. Thus, the opening 121a of the branch portion 121 can be easily displaced so as to be at an appropriate position with respect to the vessel opening of the branch vessel V2.

As long as the opening 121a of the branch portion 121 can be displaced accompanying deformation of the position adjustment portions 13, for example, the position adjustment portions 13 may be composed only of a deformable portion, or may be configured so as to include a flat portion between the deformable portion and the branch portion 121 connected to each other. In addition, the position adjustment portions 13 may be formed so as to be directly connected to an edge portion of the branch portion 121 (in this embodiment, a portion connected to the concave portion 122 in the branch portion 121). That is, the position adjustment portions 13 are disposed on the periphery (more preferably, vicinity) of the opening 121a (side opening) of the branch portion 121 and only needs to be configured such that a force for displacing the opening 121a can preferably act on the branch portion 121 as a portion where the opening 121a is formed.

In this way, the opening 121a as the side opening and the position adjustment portions 13 are disposed in a region (concave portion 122) to which the second stent graft 50 different from the first stent graft 10 on the graft portion 12 is connected.

Herein, when the concave portion 122 is formed on the graft portion 12 as in this embodiment, there is a risk that the bottom face of the concave portion 122 is displaced outward in the radial direction due to the bloodstream depending on a shape of the concave portion 122, arrangement and strength of the thin metal wires of the skeleton portion 11, or the like. In particular, when the position adjustment portions 13 in the pleated shape are provided, the pleated portion expands outward in the radial direction due to the bloodstream, and the bottom face of the concave portion 122 tends to be displaced outward in the radial direction. In this case, since the opening 121a of the branch portion 121 is also displaced, the arrangement deviates from the designed arrangement. Thus, a deformation restriction portion 14 for restricting deformation of the concave portion 122 of the graft portion 12 is disposed on the first stent graft 10 to solve the aforementioned problems.

In this embodiment, the deformation restriction portion 14 is composed of wire rods spanned in the width direction of the concave portion 122. In FIG. 2A and FIG. 2B, each of wire rods is disposed on each side of the branch portion 121 in the axial direction of the first stent graft 10. The wire rod is preferably made of e.g. a material that does not have stretchability and elasticity or has relatively low stretchability and elasticity. The deformation restriction portion 14 may be any member that can maintain the concave portion 122 in a flat shape and keep a width of the concave portion 122 constant, and the number or the like of the wire rods is not particularly limited. Furthermore, the deformation of the concave portion 122 may be restricted by a form other than the wire rod.

Since the width of the concave portion 122 is kept constant by the deformation restriction portion 14, the flatness of the bottom face of the concave portion 122 is maintained without bulging of the pleated position adjustment portions 13 due to bloodstream. As a result, the position of the branch portion 121 is kept.

FIG. 4A and FIG. 4B are diagrams illustrating a method for placing the first stent graft 10 and the second stent graft 50 in a blood vessel. FIG. 4A and FIG. 4B illustrate a case where the first stent graft 10 is placed on a lesion site of the main vessel V1 (e.g. site having an aortic aneurysm or the like) and the second stent graft 50 is placed in the branch vessel V2 branching from the main vessel V1 in the vicinity of the lesion site. The second stent graft 50 is connected to the branch portion 121 of the first stent graft 10.

An outer diameter of the expanded second stent graft 50 is equal to or greater than an inner diameter of the branch portion 121 of the first stent graft 10. In addition, since the configuration of the second stent graft 50 is substantially the same as that of the first stent graft 10 except that the second stent graft 50 does not have the branch portion 121, the concave portion 122, the position adjustment portions 13 and the deformation restriction portion 14, and explanation of the second stent graft 50 is omitted.

When the first stent graft 10 and the second stent graft 50 are placed in the blood vessel, for example, the stent graft placement device 1 is introduced into the blood vessel along the guide wire previously inserted into the blood vessel, and the distal portion of the stent graft placement device 1 is delivered to a predetermined lesion site. When pulling out the sheath 20 in this state, the first stent graft 10 is released from the sheath 20. The released first stent graft 10 expands by a self-expanding force and is placed in close contact with the main vessel V1 (see FIG. 4A).

Then, for example, the guide wire for placing the second stent graft 50 is passed through the opening 121a of the branch portion 121 of the first stent graft 10 from the branch vessel V2, and pulled out from the stent graft insertion site (e.g. groin). The stent graft placement device 1 is introduced into the blood vessel along the guide wire, and the distal portion of the stent graft placement device 1 is delivered to a predetermined site of the branch vessel V2 through an inside of the first stent graft 10. The branch portion 121 of the first stent graft 10 and the second stent graft 50 are positioned so as to overlap each other, and in this state, the sheath 20 is pulled out, so that the second stent graft 50 is released from the sheath 20. The released second stent graft 50 expands by a self-expanding force and is placed in close contact with the branch vessel V2 (see FIG. 4B).

Thereby, on the overlapping portion, the inner peripheral face of the first stent graft 10 (branch portion 121) and the outer peripheral face of the second stent graft 50 come into close contact with each other, so that the first stent graft 10 and the second stent graft 50 are connected to each other.

The second stent graft 50 may be transferred through the branch vessel V2 and inserted into the branch portion 121 of the first stent graft 10.

Figure 5A:
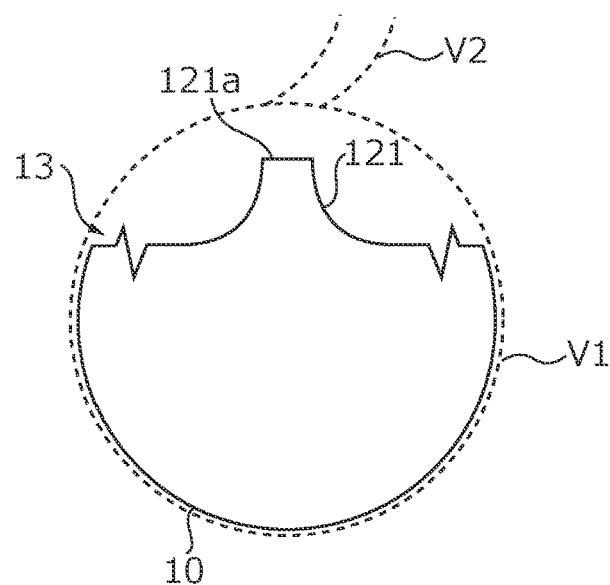
FIG. 5A is a diagram illustrating a positional relationship between an opening of a branch portion and a vessel opening of a branch vessel when the first and second stent grafts are placed in a blood vessel.
Figure 5B:
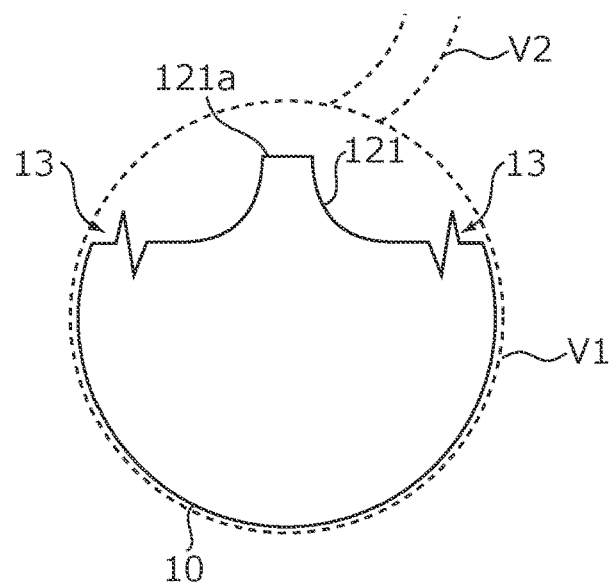
FIG. 5B is a diagram illustrating the positional relationship between the opening of the branch portion and the vessel opening of the branch vessel when the first and second stent grafts are placed in the blood vessel.
Figure 5C:
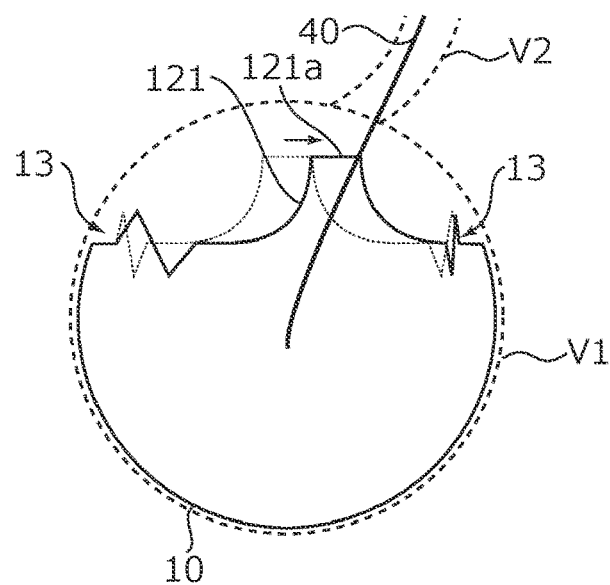
FIG. 5C is a diagram illustrating the positional relationship between the opening of the branch portion and the vessel opening of the branch vessel when the first and second stent grafts are placed in the blood vessel.

FIG. 5A to FIG. 5C are diagrams illustrating a positional relationship between the opening 121a of the branch portion 121 and the vessel opening of the branch vessel V2 when the first stent graft 10 is placed in the main vessel V1 (e.g. aorta) and the second stent graft 50 is placed in the branch vessel V2. In FIG. 5A to FIG. 5C, the main vessel V1 and the branch vessel V2 are indicated by dashed lines. Additionally, in FIG. 5C, states of the branch portion 121 and the position adjustment portions 13 before displacement are indicated by dashed lines.

As illustrated in FIG. 5A, if the opening 121a of the branch portion 121 and the vessel opening of the branch vessel V2 are arranged to be opposite to each other when placing the first stent graft 10 in the main vessel V1, the second stent graft 50 can be smoothly transferred to the indwelling site.

On the other hand, as illustrated in FIG. 5B, if the opening 121a of the branch portion 121 is displaced with respect to the vessel opening of the branch vessel V2 e.g. in the circumferential direction of the main vessel V1 when placing the first stent graft 10 in the main vessel V1, the second stent graft 50 could not have been smoothly transferred to the indwelling site in conventional cases. In contrast, since the first stent graft 10 according to this embodiment has the position adjustment portions 13, the guide wire 40 or the sheath 20 for placing the second stent graft 50 is passed through the opening 121a so as to abut on the edge portion of the opening 121a of the branch portion 121, for example, so that an external force acts on the branch portion, and therefore the opening 121a of the branch portion 121 can be displaced in the width direction (see FIG. 5C). At this time, one position adjustment portion 13 (right side in FIG. 5C) contracts in the width direction, and the other position adjustment portion 13 (left side in FIG. 5C) expands in the width direction. Thereby, the opening 121a of the branch portion 121 and the vessel opening of the branch vessel V2 can be easily aligned.

In this way, the first stent graft 10 according to this embodiment is placed in the main vessel V1 (tubular tissue), and includes the skeleton portion 11; the tubular graft portion 12 disposed along the skeleton portion 11, and having the opening 121a (side opening) leading to the lumen in a part of the tube wall; and the position adjustment portions 13 capable of adjusting a relative position of the opening 121a on the graft portion 12 while the first stent graft 10 is placed in the main vessel V1.

In the first stent graft 10 according to this embodiment, the relative position of the opening 121a of the branch portion 121 on the graft portion 12 can be adjusted by the position adjustment portions 13, and therefore, for example, even if the opening 121a of the branch portion 121 is displaced with respect to the vessel opening of the branch vessel V2 when placing the first stent graft 10 in the main vessel V1, preferable alignment between the opening 121a of the branch portion 121 and the vessel opening of the branch vessel V2 can be performed. Thus, the bloodstream between the main vessel V1 and the branch vessel V2 can be maintained.

In addition, the position adjustment portions 13 are disposed around the opening 121a (side opening) of the branch portion 121. The opening 121a of the branch portion 121 can be preferably displaced by the position adjustment portions 13 disposed around the opening 121a, and preferable alignment between the opening 121a of the branch portion 121 and the vessel opening of the branch vessel V2 can be performed.

In addition, the opening 121a of the branch portion 121 and the position adjustment portions 13 are disposed in a region to which the second stent graft 50 different from the first stent graft 10 on the graft portion 12 is connected.

Thereby, the opening 121a of the branch portion 121 can be easily displaced by the position adjustment portions 13 disposed in the region to which the second stent graft 50 is connected, so that the connection of the second stent graft 50 can be facilitated and the second stent graft 50 can be properly placed in the branch vessel V2.

In addition, the graft portion 12 has the concave portion 122 in which a part of the tube wall is recessed inward in the radial direction, and the opening 121a (side opening) and the position adjustment portions 13 are disposed on the concave portion 122. Specifically, the opening 121a is disposed on the branch portion 121 formed so as to protrude outward in the radial direction from the bottom face of the concave portion 122.

Thereby, in performing preferable connection between the first stent graft 10 and the second stent graft 50, the opening 121a of the branch portion 121 can be displaced by the position adjustment portions 13 disposed on the concave portion 122 even if the concave portion 122 having the branch portion 121 is formed, and therefore more preferable alignment between the opening 121a of the branch portion 121 and the vessel opening of the branch vessel V2 can be performed.

Furthermore, the first stent graft 10 includes the deformation restriction portion 14 for restricting deformation of the concave portion 122. Thereby, the bottom face of the concave portion 122 can be prevented from being displaced outward in the radial direction due to the bloodstream. In particular, the deformation restriction portion 14 makes it possible to prevent the opening 121a from being displaced to an unintended position even in a configuration that the relative position of the opening 121a on the graft portion 12 can be adjusted by the position adjustment portions 13. Consequently, more preferable alignment between the opening 121a of the branch portion 121 and the vessel opening of the branch vessel V2 can be performed.

In addition, the position adjustment portions 13 are formed in a pleated shape around the opening 121a of the branch portion 121. When the pleated position adjustment portions 13 expand or contract in a direction orthogonal to the extending direction of the pleats, the opening 121a of the branch portion 121 can be easily displaced, and preferable alignment between the opening 121a of the branch portion 121 and the vessel opening of the branch vessel V2 can be performed. In particular, the pleated position adjustment portions 13 are formed along the axial direction of the first stent graft 10, so that the opening 121a of the branch portion 121 can be easily displaced in the width direction.

As described above, the invention made by the present inventors has been specifically explained on the basis of the embodiments, but the present invention is not limited to the above embodiments, and can be modified without departing from the gist of the invention.

For example, in this embodiment, although the case where the position adjustment portions 13 are disposed on the graft portion 12 has been explained, the position adjustment portions 13 may be disposed on a site other than the graft portion 12. For example, the first stent graft 10 may be configured such that the position of the opening 121a of the branch portion 121 can be adjusted by devising a shape and a caulking shape of the skeleton portion 11 around the portion to which the second stent graft 50 is connected in the skeleton portion 11.

For example, in this embodiment, although the case where the position adjustment portions 13 have a pleated shape has been explained, the position adjustment portions 13 may have another shape. For example, also when portions corresponding to the pleated position adjustment portions 13 in the first stent graft 10 are made of an easily deformable material having elasticity different from that of the graft portion 12, the position of the opening 121a of the branch portion 121 can be adjusted by expansion and contraction of the corresponding portions in the width direction.

Additionally, in this embodiment, although the configuration in which one branch portion 121 (opening 121a) is disposed on the first stent graft 10 has been explained, the first stent graft 10 may have a plurality of (e.g. three) branch portions 121. In this case, it is preferable that the position adjustment portions 13 can adjust the position of the opening 121a of each branch portion 121. In particular, by providing one pleated position adjustment portion 13 extending along the openings 121a of the plurality of branch portions 121, the opening 121a of any one branch portion 121 among the openings 121a of the plurality of branch portions 121 (e.g. middle opening 121a among three openings) is displaced in a predetermined direction (e.g. width direction), so that the openings 121a of the other branch portions 121 can also be displaced in conjunction with the displacement of the one opening. Thereby, alignment between the openings 121a of the plurality of branch portions 121 and the vessel openings of the plurality of branch vessels V2 can be facilitated.

In addition, the position adjustment portions 13 need not be disposed along the axial direction of the first stent graft 10, and the arrangement of the position adjustment portions 13 can be arbitrarily changed as appropriate. For example, the position adjustment portions 13 are formed in one direction (width direction) orthogonal to the axial direction of the first stent graft 10, so that the opening 121a of the branch portion 121 can be easily displaced in the axial direction. In addition, the position adjustment portions 13 are arranged in a ring formation so as to surround the opening 121a of the branch portion 121, so that the opening 121a of the branch portion 121 can be easily displaced in all directions orthogonal to the axial direction of the branch portion 121.

In addition, the deformation restriction portion 14 only needs to be able to suppress deformation of the concave portion 122 and maintain the flatness of the bottom face of the concave portion 122. For example, the deformation restriction portion 14 may be configured such that the bottom face of the concave portion 122 is drawn inward in the radial direction by a string-shaped member or the like that joins a portion opposite to the bottom face of the concave portion 122 with the bottom face of the concave portion 122 on the graft portion 12.

Additionally, in this embodiment, although the configuration in which the first stent graft 10 has the concave portion 122 has been explained, this configuration is merely an example, and the present invention is not limited to this configuration. The first stent graft 10 may or may not have the concave portion 122 as appropriate. Furthermore, although the first stent graft 10 was configured to have the branch portion 121, this configuration is merely an example, the present invention is not limited to this configuration. The first stent graft 10 may or may not have the branch portion 121 as appropriate.

That is, the first stent graft 10 does not necessarily have the concave portion 122 and the branch portion 121, and it is sufficient that the position adjustment portions 13 are disposed around the opening 121a as the side opening on the graft portion 12.

In addition, the branch portion 121 may be composed of a member different from the graft portion 12 and formed so as to be joined to the graft portion 12. In this case, the branch portion 121 may be made of a material same as or different from that of the graft portion 12.

Furthermore, in this embodiment, although the stent graft to be placed in the blood vessel as an example of a tubular tissue has been explained, the present invention can also be applied to a stent graft to be placed in a tubular tissue other than blood vessels, e.g. a branch portion between a bile duct and a duodenum, or the like.

The embodiment disclosed in this specification is an example in all regards and should be regarded as unrestrictive. The scope of the present invention is stipulated not by the aforementioned explanation but by claims, and intended to include meanings equivalent to claims, and all modifications within the scope of claims.

Disclosure contents of specifications, figures, and abstracts included in Japanese Patent Application No. 2018-182618 filed on Sep. 27, 2018 are all incorporated in this application.

DESCRIPTION OF REFERENCE NUMERALS

1 Stent graft placement device
10 First stent graft
11 Skeleton portion
12 Graft portion
121 Branch portion
121a Opening (side opening)
122 Concave portion
13 Position adjustment portion
14 Deformation restriction portion
50 Second stent graft
V1 Main vessel
V2 Branch vessel

The invention claimed is:
1. A stent graft to be placed in a tubular tissue, comprising a skeleton portion,
a tubular graft portion disposed along the skeleton portion, and having a side opening leading to a lumen in a part of a tube wall,
a position adjustment portion capable of adjusting a relative position of the side opening on the graft portion in a state where the stent graft is placed in the tubular tissue, wherein
the position adjustment portion has pleats formed along an axial direction of the stent graft on both sides of the side opening in a width direction orthogonal to the axial direction, and
the pleats are creases sterically folded such crest portions and trough portions are alternately formed, and the creases are formed along the axial direction.

2. The stent graft according to claim 1, wherein the position adjustment portion is disposed around the side opening.

3. The stent graft according to claim 1, wherein the side opening and the position adjustment portion are disposed in a region to which another stent graft different from the stent graft on the graft portion is connected.

4. The stent graft according to claim 1, wherein
the tubular graft portion has a concave portion in which the part of the tube wall is recessed inward in a radial direction, and
the side opening and the position adjustment portion are disposed on the concave portion.

5. The stent graft according to claim 4, comprising a deformation restriction portion for restricting deformation of the concave portion.

6. The stent graft according to claim 4, wherein
the pleats are formed by folding the bottom face of the concave portion.

7. The stent graft according to claim 6, comprising a branch portion that is formed so as to protrude outward in the radial direction from the bottom surface of the concave portion, wherein
the side opening is disposed at the tip of the branching portion.

8. The stent graft according to claim 5, wherein
the deformation restriction portion is composed of wire rods spanned in the width direction of the concave portion.

9. The stent graft according to claim 8, wherein
each of the wire rods is disposed on each side of the branch portion in the axial direction.

10. The stent graft according to claim 1, wherein
the position adjustment portion can adjust the relative position of the side opening on the graft portion in the width direction.

* * * * *